United States Patent
Dilda et al.

(10) Patent No.: US 11,542,295 B2
(45) Date of Patent: Jan. 3, 2023

(54) USE OF 20-HYDROXYECDYSONE AND THE DERIVATIVES THEREOF IN THE TREATMENT OF MYOPATHIES

(71) Applicants: BIOPHYTIS, Paris (FR); SORBONNE UNIVERSITE, Paris (FR)

(72) Inventors: Pierre Dilda, Paris (FR); René Lafont, Paris (FR); Mathilde Latil, Paris (FR); Maria Serova, Nozay (FR); Onnik Agbulut, Issy-les-Moulineaux (FR); Stanislas Veillet, Savigny sur Orge (FR)

(73) Assignees: BIOPHYTIS, Paris (FR); SORBONNE UNIVERSITÉ, Paris (FR)

( * ) Notice: Subject to any disclaimer, the term of this patent is extended or adjusted under 35 U.S.C. 154(b) by 241 days.

(21) Appl. No.: 16/609,205

(22) PCT Filed: Apr. 27, 2018

(86) PCT No.: PCT/EP2018/060975
§ 371 (c)(1),
(2) Date: Oct. 28, 2019

(87) PCT Pub. No.: WO2018/197708
PCT Pub. Date: Nov. 1, 2018

(65) Prior Publication Data
US 2020/0179407 A1  Jun. 11, 2020

(30) Foreign Application Priority Data

Apr. 28, 2017 (FR) ..................................... 1753775
Aug. 31, 2017 (FR) ..................................... 1758071

(51) Int. Cl.
C07J 9/00 (2006.01)
A61P 21/06 (2006.01)
A61K 31/575 (2006.01)

(52) U.S. Cl.
CPC ............... *C07J 9/00* (2013.01); *A61K 31/575* (2013.01); *A61P 21/06* (2018.01)

(58) Field of Classification Search
CPC ...... A61K 31/575; A61K 36/28; A61K 36/88; A61P 21/00; A61P 21/06; C07J 9/00
USPC ....................................................... 514/181
See application file for complete search history.

(56) References Cited

U.S. PATENT DOCUMENTS 8,785,149 B2 *  7/2014  Restifo ............... G01N 33/5058
                                                                435/32
2020/0148718 A1*  5/2020  Lafont ................... A61K 36/88

FOREIGN PATENT DOCUMENTS

FR        3 021 318 A     11/2015

OTHER PUBLICATIONS

Hirunsai et al. In Vivo, 2016, 30(6), 869-877 (Year: 2016).*
Muthita Hirunsai, et al.: "Effect of 20-Hydroxyecdysone on Proteolytic Regulation in Skeletal Muscle Atrophy", In Vivo: International Journal of Experimental and Clinical Pathophysiology and Drug Research, vol. 30, No. 6, Nov. 4, 2016, pp. 869-878, XP055457907.
Anonymous: "Biophytis presents preliminary clinical data of SARA-PK, and new preclinical data of Sarconeos for treating sarcopenia", Press Release, Biophytis, Dec. 16, 2016, pp. 1-4, XP055430042.
Anonymous: "Biophytis", Sep. 24, 2015, pp. 1-32, XP002778985.
D.M. Cheng, et al.: "Continuous infusion of 20-hydroxyecdysone increased mass of tricepts brachii in C57BL/6 mice", Phytotherapy Research, Wiley, UK, Apr. 1, 2013, pp. 107-111, XP018507464.
Li-Jun Tan, et al.: "Molecular genetic studies of gene identification for sarcopenia", Human Genetics, Springer, Berlin, DE, vol. 131, No. 1, Jun. 26, 2011, pp. 1-31, XP019992518.
International Search Report, dated Jul. 5, 2018, corresponding to International Application No. PCT/EP2018/060975.
Barnabei M.S., Martindale J.M., Townsend D., Metzger J.M. (2011). Exercise and muscular dystrophy: implications and analysis of effects on musculoskeletal and cardiovascular systems. Compr Physiol. Jul. 2011;1(3):1353-63.
Brigstock DR 2010. Connective tissue growth factor (CCN2, CTGF) and organ fibrosis: lessons from transgenic animals. J Cell Commun Signal. 4 (1): 1-4.
Bulfield G., Siller W. G., Wight P. A., Moore K. J. (1984). X chromosome-linked muscular dystrophy (mdx) in the mouse. Proc. Natl. Acad. Sci. USA 81, 1189-1192.
Ferry A, Amiridis I, Rieu M. 1992 Glycogen depletion and resynthesis in the rat after downhill running. Eur J Appl Physiol Occup Physiol 64(1): 32-35.
Ferry A, Rieu P, Le Page C, Elhabazi A, Laziri F, Rieu M. 1993. Effect of physical exhaustion and glucocorticoids (dexamethasone) on T-cells of trained rats. Eur J Appl Physiol Occup Physiol 66(5): 455-460.
Gorelick-Feldman J, MacLean D, Ilic N, Poulev A, Lila MA, Cheng D, Raskin I. 2008. Phytoecdysteroids increase protein synthesis in skeletal muscle cells. J Agric Food Chem56: 3532-3537.
Hadj-Said W, Bangratz M, Vignaud A, Chatonnet A, Butler-Browne G, Nicole S, Agbulut O, Ferry A. 2012. Effect of locomotor training on muscle performance in the context of nerve-muscle communication dysfunction. Muscle Nerve 45(4): 567-577.
Hay N and Sonenberg N. (2004). Upstream and downstream of mTOR. Genes Development 18: 1926-1945.
Huebner KD, Jassal DS, Halevy O, Pines M and Anderson JE. (2008). Functional resolution of fibrosis in mdx mouse dystrophic heart and skeletal muscle by halofuginone. Am J Physiol Heart Circ Physiol. 294(4): H1550-61.
Lafont R, Raynal S, Dioh W, Veillet S, Lepifre F, Durand JD. 2014. Produits derives de la 20-hydroxyecdysone et leur utilisation dans la préparation de médicaments. Application FR3021318 (filed May 20, 2014).

(Continued)

*Primary Examiner* — Yevgeny Valenrod
(74) *Attorney, Agent, or Firm* — Ladas & Parry LLP; Malcolm J. MacDonald

(57) ABSTRACT

The invention relates to 20-hydroxyecdysone and the derivatives thereof, for use in the treatment of genetic myopathies.

17 Claims, 7 Drawing Sheets

(56) References Cited

OTHER PUBLICATIONS

Lawrence MM. 2012. Ajuga turkestanica as a countermeasure against sarcopenia and dynapenia. Ms thesis, Appalachian State University.

Loufrani L, Dubroca C, You D, Li Z, Levy B, Paulin D et al. (2004). Absence of dystrophin in mice reduces NO-dependent vascular function and vascular density: total recovery after a treatment with the amino-glycoside gentamicin. Arterioscler. Thromb. Vasc. Biol. 24: 671-676.

Matsakas A, Yadav V, Lorca S, Narkar V. (2013). Muscle ERR gamma mitigates Duchenne muscular dystrophy via metabolic and angiogenic reprogramming. FASEB J. 27: 4004-4016.

Murphy S., Dowling P., Zweyer M., Mundegar R., Henry M., Meleady P., Swandulla D., Ohlendieck K. (2016). Proteomic analysis of dystrophin deficiency and associated changes in the aged mdx-4cv heart model of dystrophinopathy-related cardiomyopathy. J. Proteomics, 145, 24-36.

Palladino M, Gatto I, Neri V, Straino S, Smith RC, Silver M et al. (2013). Angiogenic impairment of the vascular endothelium: a novel mechanism and potential therapeutic target in muscular dystrophy. Arterioscler. Thromb. Vasc. Biol. 33: 2867-2876.

Rittié L. (2017). Method for Picrosirius Red-Polarization Detection of Collagen Fibers in Tissue Sections. Methods Mol Biol. 1627: 395-407.

Roffe S, Hagai Y, Pines M, Halevy O. (2010). Halofuginone inhibits Smad3 phosphorylation via the PI3K/Akt and MAPK/ERK pathways in muscle cells: effect on myotube fusion Exper Cell Res 316(6): 1061-1069.

Schuh RA, Jackson KC, Khairallah RJ, Ward CW, Spangenburg EE. (2012). Measuring mitochondrial respiration in intact single muscle fibers. Am J Physiol Regul Integr Comp Physiol. 302(6): R712-R719.

Shi S., Hoogaars W.M., de Gorter D.J., van Heiningen S.H., Lin H.Y., Hong C.C., Kemaladewi D.U., Aartsma-Rus A., ten Dijke P., 't Hoen P.A. (2011). BMP antagonists enhance myogenic differentiation and ameliorate the dystrophic phenotype in a DMD mouse model. Neurobiol Diseases 41(2), 353-360.

Sicinski P, Geng Y, Ryder-Cook AS, Barnard EA, Darlison MG, Barnard PJ.1989. The molecular basis of muscular dystrophy in the mdx mouse: a point mutation. Science 244(4912), 1578-1580.

Simakin SYu, Panyushkin VV, Portugalov SN, Kostina LV, Martisorov EG. 1988. Combined application of préparation Ecdysten. Science Bulletin N °2, 29-31.

Song Y, Yao S, Liu Y, Long L, Yang H, Li Q, Liang J, Li X, Lu Y, Zhu H, Zhang N. 2017. Expression levels of TGF-□1 and CTGF are associated with the severity of Duchenne muscular dystrophy. Exp Ther Med 13(4): 1209-1214.

Syrov VN. 2000. Comparative experimental investigations of the anabolic activity of ecdysteroids and steranabols. Pharm Chem Journal 34(4):193-197.

Tóth N, Szabó A, Kacsala P, Héger J, Zádor E. 2008. 20-Hydroxyecdysone increases fiber size in a muscle-specific fashion in rat. Phytomedicine 15: 691-698.

Turgeman T, Hagai Y, Huebner K, Jassal DS, Anderson JE, Genin O, Nagler A, Halevy O, Pines M. (2008). Prevention of muscle fibrosis and improvement in muscle performance in the mdx mouse by halofuginone. Neuromuscul Disord. 18(11): 857-868.

Turk R, Sterrenburg E, van der Wees CG, de Meijer EJ, de Menezes RX, Groh S, Campbell KP, Noguchi S, van Ommen GJ, den Dunnen JT, 't Hoen PA. (2006). Common pathological mechanisms in mouse models for muscular dystrophies. FASEB J. 20(1): 127-129.

Wang X, McLennan SV, Allen TJ, Twigg SM. 2010. Regulation of pro-inflammatory and pro-fibrotic factors by CCN2/CTGF in H9c2 cardiomyocytes. J Cell Comm. Signal 4: 15-23.

Yin Z., Ren J., Guo W. (2014), Sarcomeric protein isoform transitions in cardiac muscle: A journey to heart failure. Biochim Biophys Acta. 1852(1):47-52.

Rando TA. (2001). Role of nitric oxide in the pathogenesis of muscular dystrophies: a "two hit" hypothesis of the cause of muscle necrosis. Microsc. Res. Tech. 55: 223-235.

\* cited by examiner

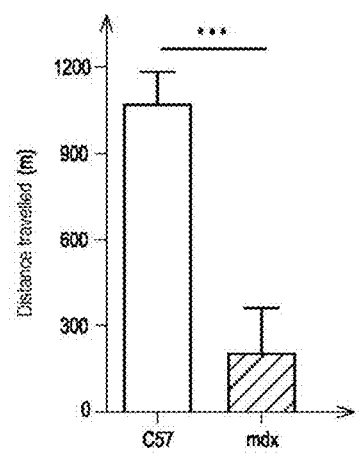
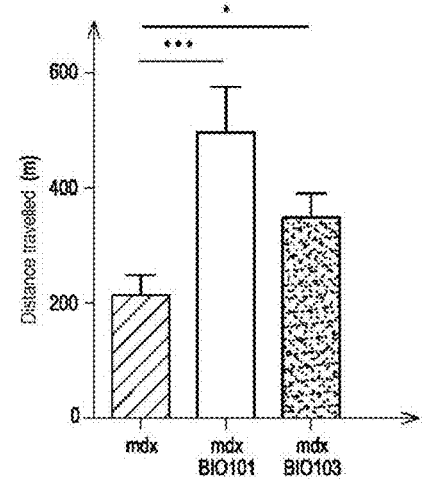
Fig. 1A          Fig. 1B
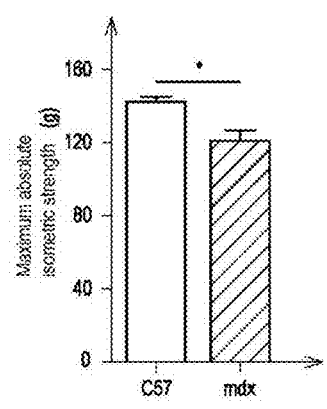
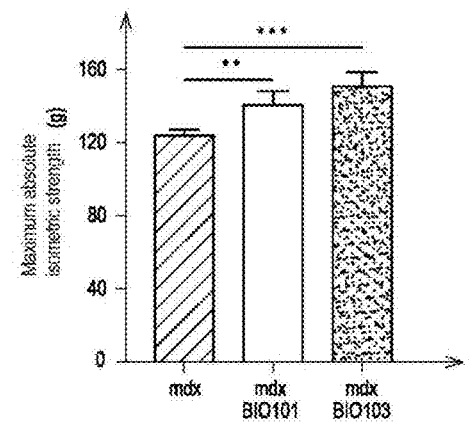
Fig. 2A          Fig. 2B

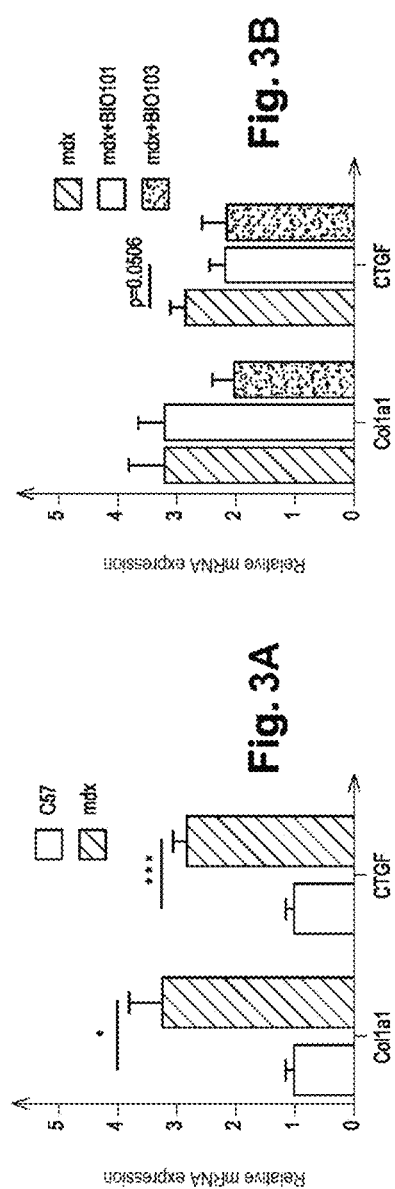
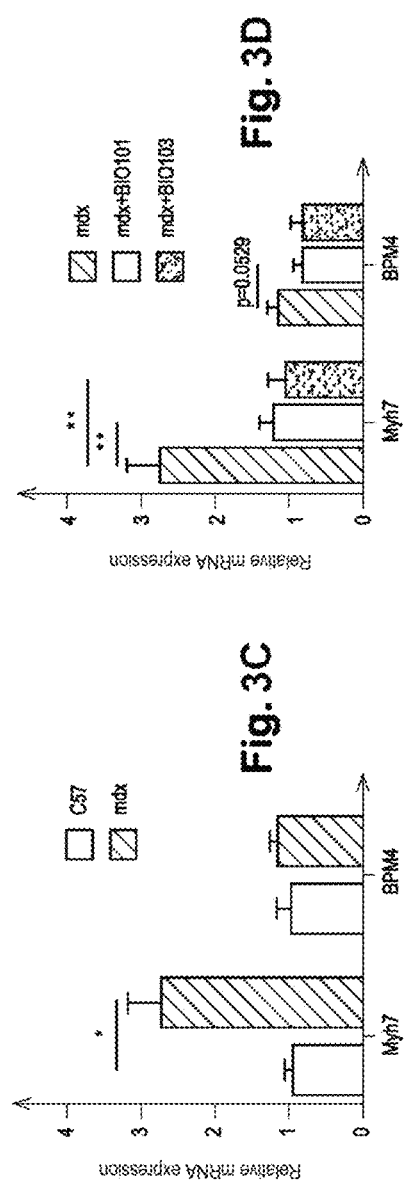

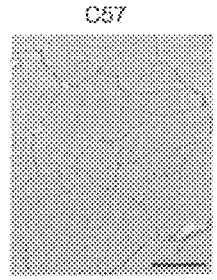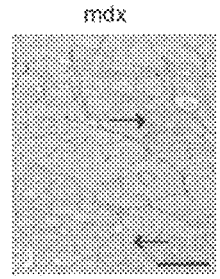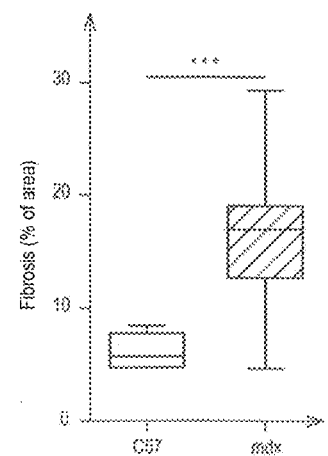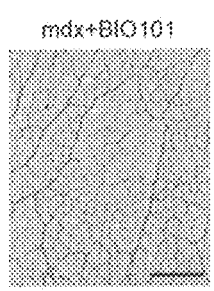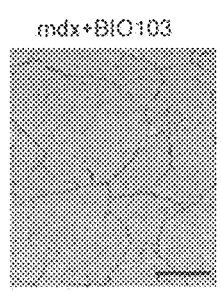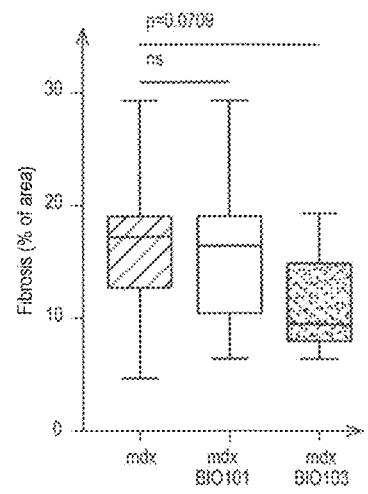

USE OF 20-HYDROXYECDYSONE AND THE DERIVATIVES THEREOF IN THE TREATMENT OF MYOPATHIES

FIELD OF THE INVENTION

The present invention relates to the use of purified natural 20-hydroxyecdysone (20E) or of synthetic derivatives for the treatment of myopathies and particularly muscular dystrophies of genetic origin.

STATE OF THE RELATED ART

Myopathies are diseases directly affecting muscle. There are different forms thereof according to the symptoms and mechanisms of muscle involvement. There are two categories: genetic myopathies and acquired myopathies.

Genetic myopathies are subdivided into:
progressive muscular dystrophies (Duchenne and Becker muscular dystrophies, limb-girdle muscular dystrophies and facioscapulohumeral dystrophy), or congenital dystrophies,
metabolic myopathies such as glycogenosis and lipidosis as well as mitochondrial myopathies,
myotonic dystrophies such as Steinert myopathy (MD1), central core, nemaline, multi-minicore congenital myopathies or centronuclear and myotubular myopathy,
Acquired myopathies include:
toxic myopathies,
inflammatory myopathies,
endocrine myopathies.

Myopathies manifest themselves as progressive or stable muscle weakness. They are generally characterised by a loss of muscle mass (atrophy). During disease progression, the muscle tissue is progressively replaced by fibrous tissue (fibrosis).

There are more than thirty forms of muscular dystrophies which particularly differ by the type of muscles affected. They are of more or less early onset and affect the skeletal muscles of different parts of the body. In some cases, progressive respiratory and cardiac muscle damage reduces patients' life expectancy.

Several tens of different genes are involved in muscular dystrophies. Most often, these are the genes responsible for the synthesis of proteins situated in the membrane of muscle cells or bound thereto and essential for maintaining structure and for muscle function. By way of example:
dystrophin is involved in Duchenne muscle dystrophy (DMD) and Becker muscle dystrophy (BMD),
calpain, dysferlin and sarcoglycans are involved in limb-girdle muscular dystrophies,
merosin, alpha-dystroglycan or selenoprotein N are involved in the case of congenital muscular dystrophies (CMD).

DMD is the most frequent form of muscular dystrophy. It affects 1 out of every 3,500 boys and is the result of mutations affecting the dystrophin gene, located on the X chromosome. A less severe form, BMD, also involves the dystrophin gene and affects 1 out of every 18,000 boys. DMD is a serious genetic condition affecting the entire muscle structure. In this disease, muscle fibre fragility leads to their destruction inducing muscle tissue necrosis. When the regeneration mechanisms are overburdened, degeneration takes over inducing a loss of muscle strength and exertion intolerance (Barnabei et al. 2011). Muscle fibres are then replaced by connective tissue (fibrosis). Muscle weakness progressively reaches the lower limbs of children over 3 years of age. The disease subsequently develops in the muscles of the back, upper limbs and finally the respiratory muscles.

There is currently no curative treatment for DMD and BMD, but orthopaedic and respiratory palliative treatments improve quality of life and life-threatening risk. Patient treatment is currently based on optimising their muscle capacities as well as on cardiac and respiratory complication prevention and treatment. The use of corticosteroids helps prolong the walking period by two years on average. However, However, some children do not respond to this treatment which further causes adverse effects, particularly significant bone weakening. Partial cardiac protection is obtained by means of a combination of converting enzyme inhibitors and beta-blockers.

New treatments are at the clinical development stage. Exon skipping consists of forcing the cell to produce a shorter, but nonetheless functional, version of dystrophin than the normal protein. A further approach of the same type consists of overriding a mutation which interrupts dystrophin synthesis prematurely. However, this type of therapy is only aimed at a small number of patients, according to the exact nature of the mutations causing their disease. Finally, gene therapy, which offers the possibility of synthesising short versions of dystrophin (mini-dystrophins or micro-dystrophins) in patients, is faced with a major problem of immune response against these proteins considered to be extraneous by the body.

Besides an irreversible decrease in appendicular muscle strength and the onset of exertion intolerance, one of the major complications of the disease is the onset of fibrosis which particularly affects the heart leading to heart failure (accompanied by dilated hypertrophy). This damage is life-threatening for patients. The onset of fibrosis is consequently an irreversible development which should be blocked in order to preserve muscle function. In this sense, therapeutic approaches must focus their efforts on:
maintaining exertion tolerance
maintaining muscle strength
and preventing the onset of fibrosis.

Phytoecdysteroids represent a major family of polyhydroxylated sterols. These molecules are produced by various plant species (ferns, gymnosperms, angiosperms) and are involved in the defence of these plants against pests.

The patent FR3 021318 discloses that phytoecdysteroids, and more particularly 20-hydroxyecdysone (20E), have been the subject of numerous pharmacological studies. These studies have highlighted the antidiabetic and anabolising properties of this molecule. The stimulant effects thereof on protein syntheses in muscles are observed in rats in vivo (Syrov et al., 2000; Tóth et al., 2008; Lawrence et al., 2012) and on C2C12 mouse myotubes in vitro (Gorelick-Feldman et al., 2008). This consists of an effect at translation level, which involves the phosphorylation of ribosomal protein p70S6K, following a cascade involving protein kinase Akt/PkB, a pathway also used by IGF-1 for stimulating protein synthesis.

Some of the effects described above in animal models have been observed in even less numerous clinical studies. Thus, 20-hydroxyecdysone increases muscle mass in young athletes (Simakin et al., 1988).

Finally, the French patent FR3021318 describes the use of 20-hydroxyecdysone and the derivatives thereof, for the treatment and prevention of sarcopenia and sarcopenic obesity (Lafont et al. 2017).

SUBJECT MATTER OF THE INVENTION

The inventors discovered that 20-hydroxyecdysone and the derivatives thereof significantly enhance the in-toto physical performances as well as the in-situ muscle strength of mammals suffering from myopathy. In-toto physical performances and in situ muscle strength are determined respectively by measuring the maximum distance travelled and by the maximum absolute isometric strength of the tibialis anterior muscle. These effects make it possible to enhance mobility in mammals suffering from myopathy and particularly muscular dystrophies.

The present invention relates to 20-hydroxyecdysone and the derivatives thereof intended to be used in the treatment of myopathy resulting from a genetic alteration.

Hereinafter in the description, the term 20-hydroxyecdysone and the derivatives thereof denotes 20-hydroxyecdysone, the derivatives, plant extracts rich in 20-hydroxyecdysone and the derivatives thereof, and compositions containing by way of active agent 20-hydroxyecdysone, the derivatives thereof and/or plant extracts rich in 20-hydroxyecdysone and the derivatives thereof.

The derivatives of 20-hydroxyecdysone are obtained by hemisynthesis.

20-hydroxyecdysone and the derivatives thereof are advantageously purified to pharmaceutical grade.

More particularly, the invention relates to 20-hydroxyecdysone and the derivatives thereof, intended to be used in the treatment of conditions resulting from muscle function impairment induced by a genetic myopathy.

The muscle function is that of the striated skeletal muscle or myocardium.

More particularly, the muscle function impairment is myocardial hypertrophy.

Even more particularly, the invention relates to 20-hydroxyecdysone and the derivatives thereof, intended to be used in the treatment of any myopathy wherein the muscle function is at least in part impaired by the progressive onset of fibrosis.

The invention relates to 20-hydroxyecdysone and the derivatives thereof, intended to be used in the treatment of myopathy resulting from a genetic alteration.

By genetic alteration is understood a mutation, a nucleotide insertion or a nucleotide deletion.

The invention relates to 20-hydroxyecdysone and the derivatives thereof, intended to be used in the treatment for example of Duchenne muscular dystrophy (DMD) and/or Becker muscular dystrophy (BMD).

According to the invention, 20-hydroxyecdysone and the derivatives thereof, are intended to be used in the treatment of any myopathy resulting from a dystrophin gene mutation.

According to one feature, 20-hydroxyecdysone is a compound of formula (I):

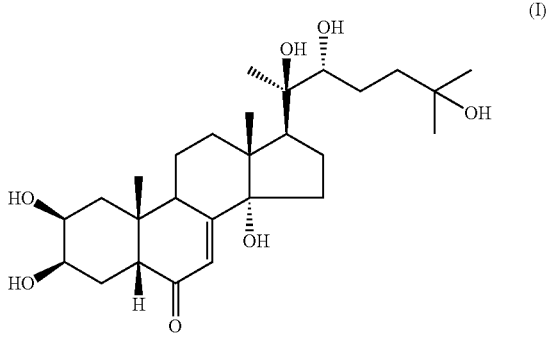 [SMILES: CC(C)(O)CC[C@@H](O)[C@](C)(O)[C@H]1CC[C@@]2(O)C3=CC(=O)[C@@H]4C[C@@H](O)[C@@H](O)C[C@]4(C)C3CC[C@]12C]

(I)

Advantageously, the compound of formula (I) is purified to pharmaceutical grade.

Particularly, the 20-hydroxyecdysone is an extract of a plant or from a part of a plant, said plant being chosen from plants containing at least 0.5% 20-hydroxyecdysone of formula (I) in dry weight of said plant, said extract comprising at least 95%, and preferably at least 97%, 20-hydroxyecdysone of formula (I).

Reference is made to purification to pharmaceutical grade.

The extract is hereinafter referred to as BIO101. It remarkably comprises between 0 and 0.05%, in dry weight of the extract, of impurities, such as minor compounds, liable to affect the safety, availability or efficacy of a pharmaceutical application of said extract.

According to a feature of the invention, the impurities are compounds with 19 or 21 carbon atoms, such as Rubrosterone, Dihydrorubrosterone or Poststerone.

The plant from which BIO101 is produced is advantageously chosen from *Stemmacantha carthamoides* (also referred to as *Leuzea carthamoides*), *Cyanotis arachnoidea* and *Cyanotis vaga*.

The invention especially focuses on the use of a Stemmacantha carthamoides root extract comprising least 95%, and preferably at least 97%, 20-hydroxyecdysone of formula (I).

In this extract, 20-hydroxyecdysone is purified to pharmaceutical grade.

More particularly, the extract is administered at a rate of 3 to 15 mg/kg*day.

Most particularly, the extract is administered at a rate of 200 to 1000 mg/day, in one or a plurality of doses, for an adult patient, and a dose of 70 to 350 mg/day, in one or a plurality of doses, for a child.

Furthermore, the invention relates to a composition comprising B10101 by way of active agent.

The composition preferably contains between 200 and 1000 mg of active agent (BIO101).

According to a further feature, a derivative of 20-hydroxyecdysone is a compound of general formula (II):

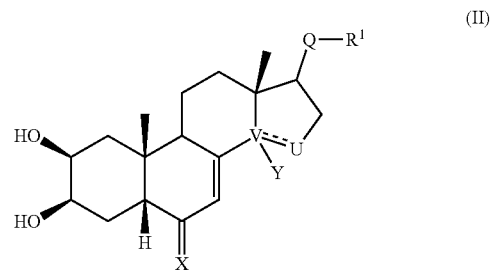

(II)

wherein:
V-U is a single carbon-carbon bond and Y is a hydroxyl group or a hydrogen, or
V-U is a C=C ethylene bond;
X is an oxygen,
Q is a carbonyl group;
$R^1$ is chosen from: a group $(C_1$-$C_6)W(C_1$-$C_6)$; a group $(C_1$-$C_6)W(C_1$-$C_6)W(C_1$-$C_6)$; a group $(C_1$-$C_6)W(C_1$-$C_6)CO_2$ $(C_1$-$C_6)$; a group $(C_1$-$C_6)A$, A representing a heterocycle optionally substituted by a group of the type OH, OMe, $(C_1$-$C_6)$, $N(C_1$-$C_6)$, $CO_2(C_1$-$C_6)$; a $CH_2Br$ group;

W being a heteroatom chosen from N, O and S, preferably O and even more preferentially S.

More particularly, in formula (II):
Y is a hydroxyl group;
$R^1$ is chosen from: a group $(C_1-C_6)W(C_1-C_6)$; a group $(C_1-C_6)W(C_1-C_6)W(C_1-C_6)$; a group $(C_1-C_6)W(C_1-C_6)CO_2(C_1-C_6)$; a group $(C_1-C_6)A$, A representing a heterocycle optionally substituted by a group of the type OH, OMe, $(C_1-C_6)$, $N(C_1-C_6)$, $CO_2(C_1-C_6)$;
W being a heteroatom chosen from N, O and S, preferably O and even more preferentially S.

In particular, the compounds of formula (II) are chosen from:

No. 1: (2S,3R,5R,10R,13R,14S,17S)-2,3,14-trihydroxy-10,13-dimethyl-17-(2-morpholinoacetyl)-2,3,4,5,9,11,12,15,16,17-decahydro-1H-cyclopenta[a]phénanthren-6-one, No. 2: (2S,3R,5R,10R,13R,14S,17S)-2,3,14-trihydroxy-17-[2-(3-hydroxypyrrolidin-1-yl)acetyl]-10,13-dimethyl-2,3,4,5,9,11,12,15,16,17-decahydro-1H-cyclopenta[a]phenanthren-6-one;

No. 3: (2S,3R,5R,10R,13R,14S,17S)-2,3,14-trihydroxy-17-[2-(4-hydroxy-1-piperidyl)acetyl]-10,13-dimethyl-2,3,4,5,9,11,12,15,16,17-decahydro-1H-cyclopenta[a]phenanthren-6-one;

No. 4: (2S,3R,5R,10R,13R,14S,17S)-2,3,14-trihydroxy-17-[2-[4-(2-hydroxyethyl)-1-piperidyl]acetyl]-10,13-dimethyl-2,3,4,5,9,11,12,15,16,17-decahydro-1H-cyclopenta[a]phenanthren-6-one;

No. 5: (2S,3R,5R,10R,13R,14S,17S)-17-[2-(3-dimethylaminopropyl(methyl)amino)acetyl]-2,3,14-trihydroxy-10,13-dimethyl-2,3,4,5,9,11,12,15,16,17-decahydro-1H-cyclopenta[a]phenanthren-6-one;

No. 6: 2-[2-oxo-2-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]ethyl sulfanylacetate;

No. 7: (2S,3R,5R,10R,13R,14S,17S)-17-(2-ethylsulfanylacetyl)-2,3,14-trihydroxy-10,13-dimethyl-2,3,4,5,9,11,12,15,16,17-decahydro-1H-cyclopenta[a]phenanthren-6-one;

No. 8: (2S,3R,5R,10R,13R,14S,17S)-2,3,14-trihydroxy-17-[2-(2-hydroxyethylsulfanyl)acetyl]-10,13-dimethyl-2,3,4,5,9,11,12,15,16,17-decahydro-1H-cyclopenta[a]phenanthren-6-one.

Most particularly, the phytoecdysteroid is a compound of formula (III):

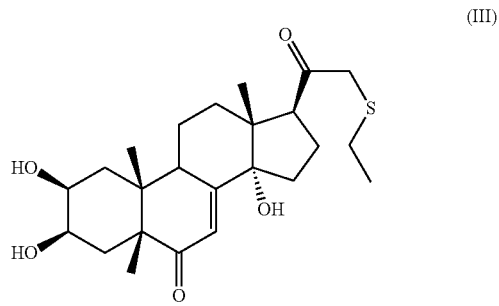 [SMILES: CCSCC(=O)[C@H]1CC[C@@]2(O)C3=CC(=O)[C@]4(C)C[C@@H](O)[C@@H](O)C[C@]4(C)C3CC[C@]12C]

(III)

This compound is hereinafter referred to as BIO103.

BRIEF DESCRIPTION OF THE FIGURES

Further advantages, aims and particular features of the present invention will emerge from the following non-limiting description of at least one particular embodiment of the devices according to the present invention, with reference to the appended drawings, wherein:

FIG. 1A is a representative diagram of the exertion tolerance of groups of mice from the C57BL10 gene pool: healthy (C57) and untreated mdx (mutated on the dystrophin gene), FIG. 1B is a representative diagram of the exertion tolerance of the groups of mice: untreated mdx, mdx treated with BIO101 and mdx treated with BIO103 after two months of treatment, FIG. 2A is a representative diagram of the maximum absolute isometric strength of the tibialis anterior muscle of the groups of mice from the C57BL10 gene pool: healthy (C57) and untreated mdx, FIG. 2B is a representative diagram of the maximum absolute isometric strength of the tibialis anterior muscle of the groups of mice: untreated mdx, mdx treated with BIO101 and mdx treated with BIO103 after two months of treatment, FIGS. 3A and 3B are representative diagrams of the genic expression (mRNA) of the fibrosis markers CTGF (connective tissue growth factor) and Col1a1 (collagen 1) from the heart of various groups of mice from the C57BL10 gene pool: healthy (C57), untreated mdx, mdx treated with BIO101 and mdx treated with BIO103, after two months of treatment, FIGS. 3C and 3D are representative diagrams of the genic expression (mRNA) of the hypertrophy markers myh7 (beta myosin heavy chain) and BMP4 (bone morphogenetic protein 4) from the heart of various groups of mice from the C57BL10 gene pool: healthy (C57), untreated mdx, mdx treated with BIO101 and mdx treated with BIO103, after two months of treatment.

FIGS. 5A and 6B are representative histological sections of tibialis anterior muscle stained with Sirius Red (SR) of the groups of healthy (C57) and untreated mdx (mdx) mice from the C57BL10 gene pool, respectively, FIG. 5C is a representative diagram of the quantification of the fibrotic zones of the groups of healthy (C57) and untreated mdx (mdx) mice from the C57BL10 gene pool, FIGS. 5D and 5E are representative histological sections of tibialis anterior muscle stained with Sirius Red (SR) of the groups of mdx mice treated with BIO101 (mdx BIO101) and mdx mice treated with BIO103 (mdx BIO103), FIG. 5F is a representative diagram of the quantification of the fibrotic zones of the groups of mdx mice treated with BIO101 (mdx BIO101) and mdx mice treated with BIO103 (mdx BIO103), FIG. 6B shows the protein expression, detected by Western Blot, of the same fibrosis marker of the gastrocnemius muscle of the groups of mice of the C57BL10 gene pool: untreated mdx (mdx), mdx treated with BIO101 and mdx treated with BIO103, after two months of treatment.

DETAILED DESCRIPTION OF EMBODIMENTS OF THE INVENTION

Figure 4A:
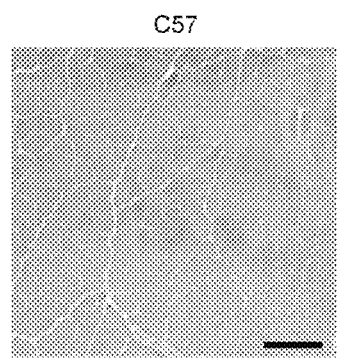
FIG. 4A is a representative image of a histological section of tibialis anterior muscle of healthy C57BL10 gene pool mice (C57), stained with haematoxylin eosin (HE)
Figure 4B:
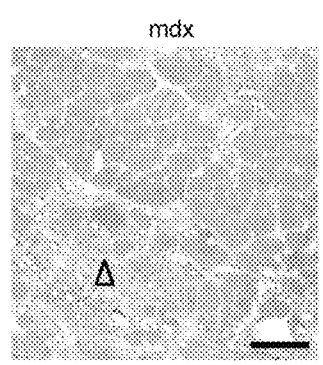
FIG. 4B is a representative image of a histological section of tibialis anterior muscle of untreated mdx C57BL10 gene pool mice (mdx), stained with haematoxylin eosin (HE)

The present description given is non-limiting.
1. BIO101 Purification Process
BIO101 is prepared from a preparation of approximately 90% pure 20-hydroxyecdysone, according to the following steps:
a) Hot dissolution of approximately 90% pure 20-hydroxyecdysone in methanol, filtration and partial concentration,
b) Addition of 3 volumes of acetone,
c) Cooling to a temperature between 0 and 5° C., with stirring,
d) Filtration of the precipitate obtained,
e) Successive rinses with acetone and water, and
f) Drying.

This purification involves a suitable recrystallisation process for this molecule capable of being carried out on an industrial scale.

The filtration of step a) is carried out by means of a 0.2 μm (micrometres) particle filter.

The partial concentration of step a) is advantageously performed by vacuum distillation, at a temperature of the order of 50° C., in the presence of MeOH.

The drying step f) is performed in a vacuum at a temperature of the order of 50° C.

2. BIO103 Synthesis Process
BIO103 is obtained by hemi-synthesis from 20-hydroxyecdysone followed by purification to pharmaceutical grade according to the following preparation process:

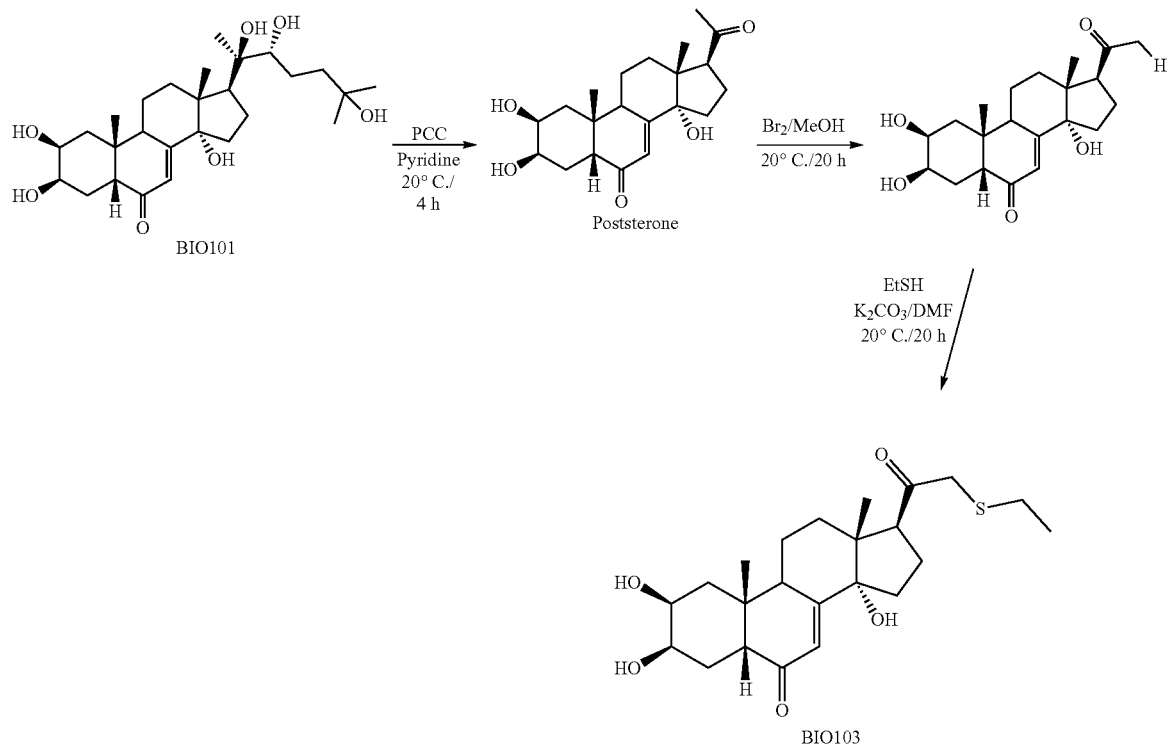

BIO103 synthesis diagram in 3 steps:
1) oxidative cleavage of the side chain of 20-hydroxyecdysone between carbons C20 and C22 to obtain poststerone (protocol known to those skilled in the art),
2) introduction of a bromine atom in position C21,
3) reaction of the brominated derivative with ethane-thiol.

3. Biological Activity of BIO101 and BIO103

While the anabolising effects of 20E present in commercial preparations have already been demonstrated in young animals, the effect of 20E in a context of a mammal suffering from myopathy wherein the progressive onset of fibrosis contributes to muscle function impairment is not known. The animal mode of Duchenne myopathy using mdx mice, from the C57BL10 gene pool, presenting with a mutation on the dystrophin gene, was used (Bulfield et al. 1984; Sicinski et al. 1989).

Twelve-week-old C57BL10 gene pool (wild mice referred to as "C57" in the figures) and C57BL10 mdx (mouse model of Duchenne muscular dystrophy, referred to as "mdx" in the figures) male mice, produced at Charles Rivers, were used. Two groups of mdx were chronically exposed per os either to BIO101 (number of mice n=9) or to BIO103 (number of mice n=9) at a dose of 50 mg/kg*day. A group of C57 mice (number of mice n=5) and a group of mdx mice (number of mice n=15) received the vehicle, i.e. no treatment. The animals of all of the groups were tested for their functional capacity (exertion tolerance test) after two months of treatment. The exertion tolerance test consists of measuring the maximum distance travelled (in-toto activity; FIGS. 1A and 1B). Furthermore, measurements of the maximum absolute isometric strength of the tibialis anterior muscle (in-situ activity; FIGS. 2A and 2B) were made after two months of treatment.

The two-month oral treatment consists of force-feeding for five days a week and in drinking water two days a week.

Exertion Tolerance Test (In-Toto Functional Study: FIGS. 1A and 1B)

The exertion tolerance test is a forced motored treadmill exercise. It is a non-invasive method for assessing in-toto skeletal function. It is gold standard method in the field (Ferry et al. 1992, 1993; Hadj-Said et al. 2012).

The acclimatisation period of the animals is at least 48 hours prior to the session during which the maximum running distance is measured. During the test, the mouse is placed in a running corridor on a motorised treadmill which enables a exercise controlled by the tester in the intensity and duration thereof. The treadmill ends with a horizontal grid which administers an electric shock (0.4 mA) if the animal is in contact for more than one second with the grid.

The running session starts with a 2-minute warm-up period during which the speed is increased from 0 to 20 cm/s. Subsequently, the running speed is increased by 5 cm/s every 10 minutes up to the limit of the peak capacities of the mouse. When it is subjected to 5 shocks in less than 10 seconds, the test is stopped. The distance travelled is noted.

As expected, it is observed that the animals presenting with a mutation on the dystrophin gene (mdx) run significantly less (−80.4%, $p<0.001$, Mann Whitney test) than the healthy animals (C57) (FIG. 1A). After two months of daily exposure (FIG. 1B), the mdx animals receiving BIO101 or BIO103 run significantly more than the mdx animals receiving the vehicle. BIO101 and BIO103 significantly improve ($p<0.001$ and $p<0.05$, respectively, unpaired t test) the distance travelled by +136% and +67%, respectively, compared to that of the untreated mdx animals (vehicle). Importantly, we demonstrate herein that treating the mdx animals with BIO101 or BIO103 partially compensates for the significant functional loss observed in the animals with a dystrophin gene mutation (mdx). The overall physical performances physiques (in-toto activity) of the animals suffering from myopathy are very significantly improved by BIO101 (2.4 fold) and BIO103 (1.7 fold).

This study demonstrates that treating with BIO101 or BIO103 results in a functional improvement characterised by a significant improvement in the exertion tolerance in an animal myopathy model (FIGS. 1A and 1B).

Maximum Absolute Isometric Strength of the Tibialis Anterior Muscle (In-Situ Functional Study: FIG. 2)

An assessment of in-situ contractility of the tibialis anterior muscle is carried out at the end of the protocol, i.e. after two months of treatment.

On the day of sacrifice, the mouse is anaesthetised with an intraperitoneal injection of pentobarbital (55 mg/kg, 0.1 mL/10 g of body weight) before measuring the in-situ strength of the tibialis anterior muscle (TA). An incision is performed on the skin on the top of the paw, revealing the tendon which is cut at the distal end thereof. The distal tendon of the TA is attached to the servomotor lever (305B Dual-Mode Lever, Aurora Scientific). An incision is performed on the skin on the side of the thigh, revealing the sciatic nerve, between 2 muscle groups. The sciatic nerve is stimulated with a bipolar electrode (supramaximal square wave pulse of 10V, 0.1 ms). The strength is measured during contractions in response to electrical stimulation (frequency of 75-150 Hz, duration of 500 ms). The temperature of the mouse is kept at 37° C. using a radiant lamp. The maximum absolute isometric tetanic strength is measured.

As expected, it is observed that the mdx animals have a significantly lower maximum absolute isometric contraction ($p<0.05$, unpaired t test) than that of the healthy C57 animals (FIG. 2A). After two months of treatment, a significant increase in the maximum absolute isometric strength of the tibialis anterior muscle is observed in the mdx animals treated with BIO101 (+15.3%, $p<0.05$, unpaired t test) and with BIO103 (+22.5%, $p<0.001$, unpaired t test) at a dose of 50 mg/kg*day compared to the mdx animals receiving the vehicle (FIG. 2B).

This study demonstrates that treating with BIO101 or BIO103 results in a functional improvement characterised by a significant increase in the maximum absolute isometric strength of the tibialis anterior muscle in an animal myopathy model (FIGS. 2A and 2B).

Myocardial Fibrosis and Cardiac Hypertrophy (Molecular Study: FIGS. 3A, 3B, 3C, 3D)

An assessment of markers of fibrosis and cardiac hypertrophy is carried out at the end of the protocol, i.e. after two months of treatment. On the day of sacrifice, the mice are euthanised by decapitation and the heart is removed then frozen immediately in liquid nitrogen. The total RNA is extracted with TRIzol® lysis Reagent (Life technologies) and a tissue homogeniser (Bio-Gen PRO200). The extract RNA is quantified by spectrophotometry then the quality thereof is verified and validated with the Experion RNA StdSens Analysis Kit (Bio-Rad). The cDNA is then synthesised with the RevertAid First Strand cDNA Synthesis Kit (Thermo Fisher Scientific). Finally, semi-quantitative PCR analysis was carried out using SYBR® Green (Roche), a DNA intercalating agent and a LightCycler® 480 Real Time PCR (Roche) apparatus on 384-well plates. The molecular markers measured are as follows:

CTGF and collagen I: connective tissue growth factor (CTGF) is associated with healing and with many pathological fibrotic processes including DMD (Brigstock 2010; Song Y. 2017). Increased genic expression of CTGF is associated with cardiac fibrosis in mdx mice (Au 2011). CTGF stimulates collagen synthesis (of which collagen 1) in cardiac fibroblasts and contributes to myocardial fibrosis (Wang 2010), myh7: increased mRNA expression of beta myosin heavy chain (myh7) is linked with cardiac hypertrophy. This embryonic isoform is expressed in the adult myocardium in response to the onset of heart failure (Yin et al. 2014). Moreover, increased myh7 expression is particularly demonstrated in DMD (Murphy et al. 2016) and in arrhythmogenic cardiomyopathy which are both characterised by cardiomyocyte loss and the onset of myocardial fibrosis (Gerçek 2017).

BMP4: bone morphogenetic protein 4 (BMP4) is an important repressor of myogenic differentiation. It interferes with the muscle regeneration process in DMD (Shi 2011).

The analysis of molecular markers linked with the onset of cardiac fibrosis in DMD confirms a significant increase in the genic expression of CTGF and collagen I (Col1a1) in mdx animals compared to healthy animals (p<0.001 and p<0.05, respectively, unpaired t test, FIG. 3A). The two-month treatment with BIO101 at a dose of 50 mg/kg*day prevents (p=0,0506, unpaired t test) the genic expression of CTGF in mdx animals treated with BIO101 compared to control mdx animals, receiving the vehicle (FIG. 3B). Treating mdx animals with BIO103 at the same dose tends to prevent the genic expression of Col1a1 compared to control mdx animals (FIG. 3B).

The genic expression of myh7 is significantly increased (p<0.05, unpaired t test) in mdx animals compared to wild C57 animals (FIG. 3C). Treating mdx animals with BIO101 and BIO103 at a dose of 50 mg/kg*day significantly reduces the expression of myh7 (p<0.01, unpaired t test) compared to mdx animals receiving the vehicle (FIG. 3D). Moreover, BIO101 reduces the genic expression of BMP4 (p=0.0529, unpaired t test) compared to control mdx animals, receiving the vehicle (FIG. 3D).

Skeletal Muscle Fibrosis (Histological Study: FIGS. 4 and 5)

An assessment of muscle fibrosis by histological study is carried out on the tibialis anterior muscle (abbreviated as TA). Histological sections (7 µm) are produced and stained either with haematoxylin eosin (HE) or with Sirius Red (SR).

Figure 4C:
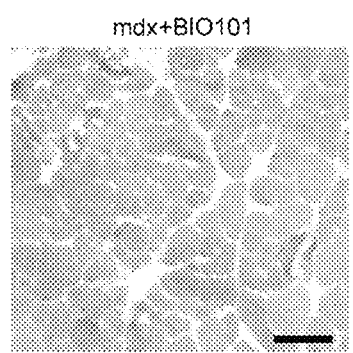
FIG. 4C is a representative image of a histological section of tibialis anterior muscle of mdx C57BL10 gene pool mice treated with BIO101 (mdx+BIO101), stained with haematoxylin eosin (HE)
Figure 4D:
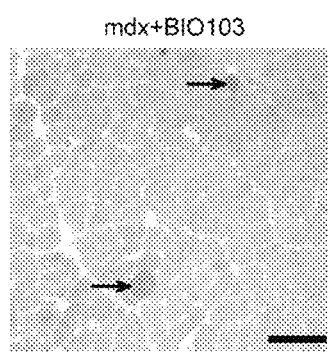
FIG. 4D is a representative image of a histological section of tibialis anterior muscle of mdx C57BL10 gene pool mice treated with BIO103 (mdx+BIO103), stained with haematoxylin eosin (HE)

An anatomopathological study of the sections of tibialis anterior muscle stained with HE makes it possible to assess the degree of muscle fibre involvement. Representative images of tibialis anterior muscle sections stained with HE obtained from C57 animals (FIG. 4A), mdx animals (FIG. 4B), mdx animals treated with BIO101 (FIG. 4C) and mdx animals treated with BIO103 (FIG. 4D) are shown. The scale bars correspond to 200 µm. The TA muscles of C57 mice show no muscle lesions (FIG. 4A). The TA muscles of untreated mdx mice show a wide diversity of lesion profiles: moderate anisocytosis with numerous necrotic fibres. Some muscles exhibit for their part pronounced to severe, multifocal, anisocytosis, with atrophy of a large proportion of myocytes, as well as large chronic inflammatory foci with associated fibrosis (FIG. 4B) and mononuclear cell infiltrates (essentially macrophages). The Δ sign indicates the inflammatory foci with which fibrosis is associated. Finally, some muscles exhibit large acute necrotic plaques. The muscles of the mice treated with BIO101 exhibit only two types of lesion profiles: a minor lesion profile with little anisocytosis, necrosis or inflammation (37.5%, 3 out of 8 TA muscles) and a pronounced lesion profile with anisocytosis, dispersed necrotic fibres and variable inflammation (62.5%, 5 out of 8 TA muscles) (FIG. 4C). Interestingly, the muscles of the mice treated with BIO103 exhibit fewer muscle lesions with a minor lesion profile. Indeed, 67% (6 out of 9 TA muscles) of the muscles treated with BIO103 can be classified in this category. In histological terms, the large majority of myocytes exhibit central nuclei (indicators of necrosis-regeneration phenomena), minimal to slight variation in size (anisocytosis), some rare necrotic and hypercontracted myocytes (initial phase of necrosis; black arrows, FIG. 4D), and some rare inflammatory cells in the endomysium. The other muscles treated with BIO103 exhibit either a pronounced lesion profile with a somewhat necrotic tendency (11% of TA muscles, 1 out of 9 TA muscles) with anisocytosis, dispersed necrotic fibres, and acute necrosis i.e. a pronounced lesion profile tending towards atrophy with significant anisocytosis, with no necrotic fibre (11%, 1 out of 9 TA muscles). Finally, one of the TA muscles exhibits a severe lesion profile with large acute necrotic plaques with no regeneration (11%, 1 out of 9 TA muscles).

An anatomopathological analysis of the sections of tibialis anterior muscle stained with SR makes it possible to quantify the fibrotic area. SR staining makes it possible to visualise fibrotic zones on the histological sections (Rite 2017). Representative images of the sections of tibialis anterior muscle stained with SR obtained from C57 animals (FIG. 5A), mdx animals (FIG. 5B), mdx animals treated with BIO101 (FIG. 5D) and mdx C57 animals treated with BIO103 (FIG. 5E) are shown. The scale bar represents 200 µm. The percentage area corresponding to fibrosis is significantly increased (p<0.001, Mann Whitney test) in the mdx group compared to the C57 group (FIG. 5C). The black arrows indicate the zones exhibiting significant muscle fibrosis. Treating mdx animals with BIO103 clearly tends to prevent (p=0.0709, unpaired t test) the onset of fibrosis compared to the control mdx group, receiving the vehicle (FIG. 5F).

Skeletal Muscle Fibrosis (Biochemical Study: FIG. 6)

Figure 6A:
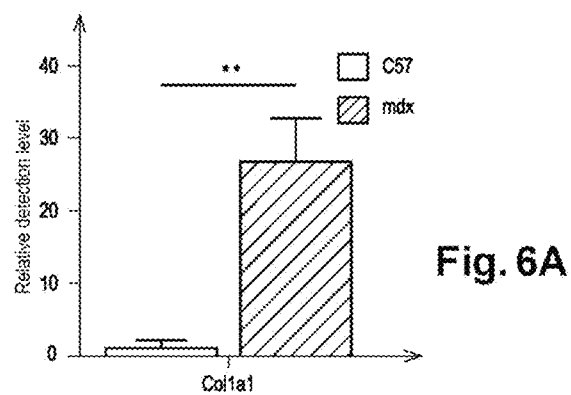
FIG. 6A shows the protein expression, detected by Western Blot, of the fibrosis marker collagen 1 (Col1a1) of the gastrocnemius muscle of the groups of mice of the C57BL10 gene pool: healthy (C57), untreated mdx (mdx)
Figure 6B:
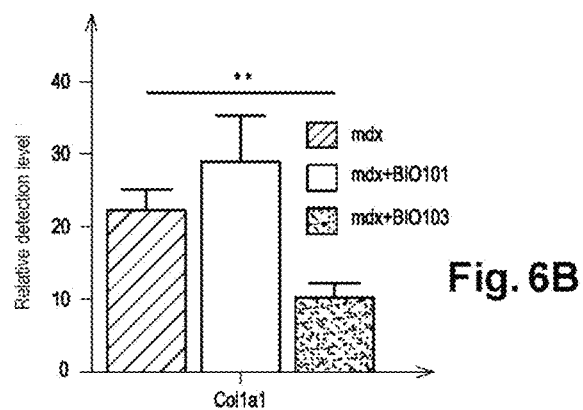

Alongside the observations made on the tibialis anterior muscle, an assessment of a marker of muscle fibrosis is carried out on the gastrocnemius muscle. The muscle is dissociated with moderate stirring for 16 h at 4° C. in RIPA lysis buffer. The proteins are assayed, resolved in SDS PAGE gel prior to being transferred to PVDF membrane. Collagen I is detected by Western Blot, detected by chemiluminescence then quantified by densitometry after normalisation with reference to GAPDH detection. As expected, the protein expression of collagen I is significantly increased (p<0.01; unpaired t test) in the gastrocnemius muscles of mdx mice compared to the muscles of healthy mice (C57). The protein expression of collagen I is increased 27-fold (FIG. 6A). Treating mdx mice with BIO103 makes it possible to observe a significant decrease (p<0.01; unpaired t test) in the protein expression of collagen I compared to untreated mdx mice (vehicle) (FIG. 6B).

Further experimental results relating to the biological activity of BIO101 and BIO103 are given in section 5 of the present description, hereinafter.

4. In Vitro Biological Activity of BIO101

Differentiation of Myoblasts into Myotubes

Sterrenburg et al. demonstrated that ineffective muscle regeneration in DMD cells is caused by impaired myoblast differentiation and deficient myotube maintenance (Turk et al., 2006). A combination of reduced proliferation, impaired fusion and deficient maintenance of DMD myotubes leads to ineffective muscle regeneration and may contribute to the severe phenotype of DMD patients.

Various parameters have been measured to assess myotube differentiation. Human DMD skeletal muscle cells (KM571DMD10FL Cl1) were differentiated for 3 days then incubated with or without BIO101 at 10 µM. The fusion index and the number of nuclei per myotube were validated as relevant and sensitive indicators of myotube differentiation.

Figure 7A:
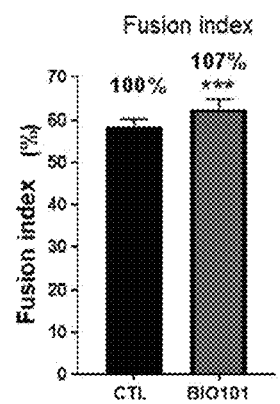
FIG. 7A is a representative diagram of the myoblast fusion index into myotubes. The human myoblasts used were obtained from patient suffering from DMD. The differentiating myoblasts were treated with BIO101 or the vehicle for 3 days.

The fusion index illustrated in FIG. 7A represents the percentage of differentiated cell nuclei with respect to the cell total.

Figure 7B:
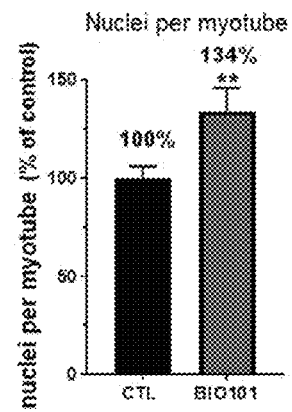
FIG. 7B is a representative diagram of the number of nuclei per myotube. The human myoblasts used were obtained from patient suffering from DMD. The differentiating myoblasts were treated with BIO101 or the vehicle for 3 days.

The number of nuclei per myotube is illustrated in FIG. 7B, 300 myotubes were counted.

Figure 7C:
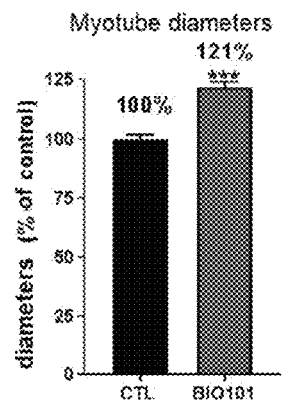
FIG. 7C is a representative diagram of the myotube diameter. The human myoblasts used were obtained from patient suffering from DMD. The differentiating myoblasts were treated with BIO101 or the vehicle for 3 days.

The myotube diameter is illustrated in FIG. 7C, 150 myotubes were measured per condition.

There is observed in the presence of BIO101 enhanced differentiation of human DMD myoblasts into myotubes (FIGS. 7A, 7B and 7C). A significant increase of +7% ($p<0.001$) of the fusion index is observed.

This is accompanied by a 34% increase ($p<0.01$) in the number of nuclei per myotube, and a 21% increase ($p<0.001$) in the myotube diameter.

The results in FIGS. 7A, 7B and 7C show the mean data measured during three independent experiments, plus or minus the standard error (SEM). The statistical analysis using a Mann-Whitney test shows a significant difference between the cells treated with BIO101 at a concentration of 10 µM (micromoles) and the untreated control cells (annotated as "CTL" in FIG. 7), $p<0.01$ (**); $p<0.001$ (*).

Signalling Pathways

The Pl3K/AKT/mTOR signalling pathway plays an essential role in cell growth, proliferation, motility, survival, apoptosis, autophagy and angiogenesis (Hay et al., 2004).

MAP kinases (abbreviated from mitogen-activated protein kinases), including ERK1 and ERK2, are involved in a variety of functions such as muscle regeneration, restructuring and contractions. In mdx mice, it has been demonstrated (Roffe et al., 2010) that activation of the Pl3K/Akt and MAPK pathways in muscle cells was particularly associated with beneficial effects (Turgeman et al., 2008; Huebner et al., 2008).

Human DMD skeletal muscle cells (KM571DMD1OFL Cl1) were differentiated for 5 days then optionally incubated with BIO101 at 10 µM for periods of between 10 minutes and 24 hours.

Figure 8A:
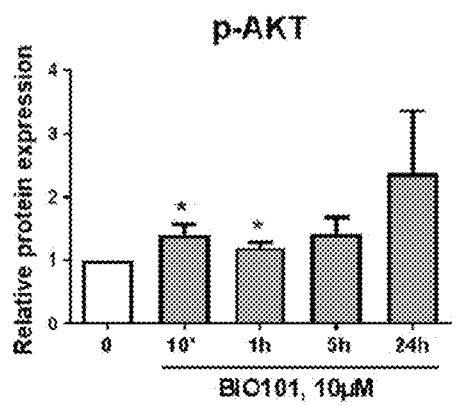
FIGS. 8A and 8B show the protein expression, detected by Western Blot, of the phosphorylated forms of the AKT and ERK1/2 proteins in human myoblasts from a patient suffering from DMD. The differentiating myoblasts were treated with BIO101 for a duration between 10 min and 24 hours.
Figure 8B:
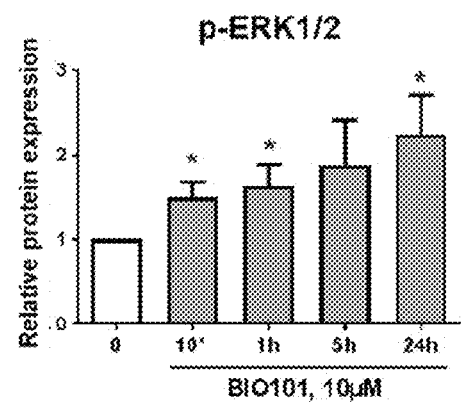

A densitometric analysis of results of at least 6 independent Western Blot experiments described the effects of BIO101 on the phosphorylation of AKT (FIG. 8A) and ERK1/2 (FIG. 8B) is shown, *$p<0.05$ versus the untreated control.

It is observed that BIO101 induces a significant increase of p-AKT and p-ERK1/2.

On reading the results shown, it is observed that BIO101 induces significant, early activation of the AKT and MAPK signalling pathways in human DMD myocytes.

Cellular Respiration

It is known that there exists a decrease in basal mitochondrial respiration in DMD muscle fibres (Schuh et al. 2015).

Interestingly, on myotubes of DMD patients, the beneficial properties of BIO101 in terms of the differentiation of the myoblasts of a DMD patient (FIG. 7) are accompanied by positive effects on the energy metabolism.

Human DMD skeletal muscle cells (KM571DMD1OFL Cl1) were differentiated for 4 days, then incubated in the presence or absence of BIO101 (1 or 5 µM) for 2 days. The oxygen consumption rate, also known as OCR, which reflects the mitochondrial respiration of the cells was measured using a Seahorse XF Analyzer (registered trademark, Agilent).

Figure 9A:
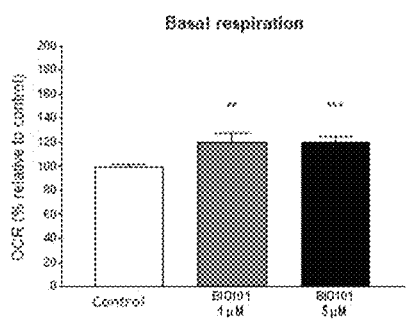
FIGS. 9A and 9B show respectively the basal and maximum respiration of human myoblasts obtained from a patient suffering from DMD. The differentiating myoblasts were treated with the vehicle or BIO101 at different doses for three days. The cell respiration is determined by measuring the oxygen consumption rate.
Figure 9B:
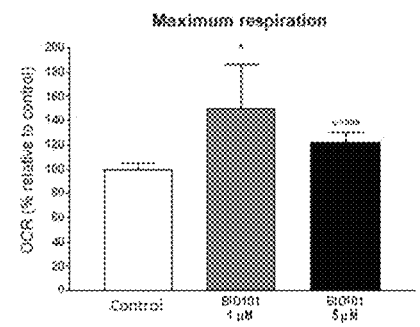

The basal respiration is measured directly whereas the maximum respiration is measured after adding oligomycin followed by FCCP (FIG. 9A and FIG. 9B). The results are referenced to the OCR of the untreated cells and are shown in the form of means plus or minus the standard error (SEM).

After two days of treatment with BIO101, it appears that a DMD patient's cells have significantly increased basal and maximum respirations compared to those of the untreated cells.

More specifically, a basal respiration increased by 20% ($p<0.01$) is observed on the cells treated with BIO101 at a dose of 1 µM. A basal respiration increased by 21% ($p<0.001$) is observed on the cells treated with BIO101 at a dose of 5 µM. A maximum respiration increased by 51% ($p<0.05$) is observed on the cells treated with BIO101 at a dose of 1 µM. A maximum respiration increased by 22% ($p=0.13$) is observed on the cells treated with BIO101 at a dose of 5 µM. The results shown are obtained from at least four independent experiments.

The Mann and Whitney statistical test made it possible to demonstrate a significant difference between the cells treated with BIO101 at 1 and 5 µM and the untreated cells, $p<0.05$ (*), <0.01 (), 0.001 (*).

BIO101 contributes to the enhancement of the energy metabolism of the muscle cells of DMD patients.

5. In Vivo Biological Activity of BIO101 and BIO103

Striated skeletal muscle is one of the body's most vascularised tissues and endothelial cells are essential for muscle regeneration processes. Dystrophin is present at the level of the smooth muscle cells of the vessels and the absence thereof may cause vascularisation disorders. Indeed, it has been demonstrated that in a DMD muscle, necrotic fibres are very often clustered and that this phenomenon was due to a reduction in the blood flow of the common capillaries to this cluster of fibres (Rando, 2001) inducing ischemic fibre necrosis.

Besides blood flow, more recent studies have demonstrated a reduction in vascular density in mdx mice (Loufrani et al., 2004; Matsakas et al., 2013). A further study also demonstrated that angiogenesis was impaired in the mdx mouse model (Palladino et al., 2013). These studies show that there is a rationale indicating that there is a vascularisation defect in DMD whether in terms of the quality thereof, quantity thereof as well as in terms of angiogenesis, and that the muscle tissue is placed under ischemic conditions.

Skeletal Muscle Vascularisation

A quantitative vascularisation study was carried out on sections of tibialis anterior muscle (abbreviated as TA) of healthy C57 mice as well as on mdx mice treated with the vehicle and mdx mice treated with BIO101 or BIO103. Double immunofluorescence labelling is carried out, anti-laminin labelling with the function of identifying the basal membrane of the muscle fibres and anti-CD31 labelling having the function of identifying the vessel. The number of vessels per muscle fibre is quantified.

Figure 10A:
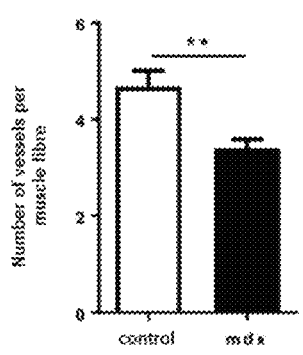
FIG. 10A is a representative diagram of the quantification of blood vessels surrounding each muscle fibre of the groups of healthy (C57) and untreated mdx C57BL10 gene mice.

As expected, it is observed that the animals exhibiting a mutation on the dystrophin gene (mdx) have a reduced number of vessels per muscle fibre. The reduction observed is 27.2% ($p<0.01$) compared to healthy animals (C57) (FIG. 10A).

Figure 10B:
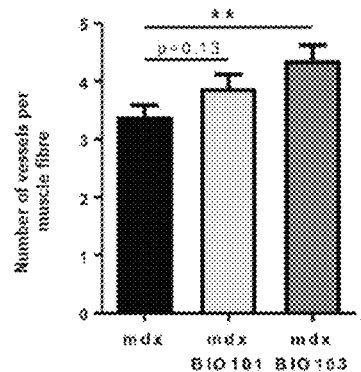
FIG. 10B is a representative diagram of the quantification of blood vessels surrounding each muscle fibre of the groups of mdx mice treated with the vehicle (mdx), BIO101 (mdx BIO101) and mdx mice treated with BIO103 (mdx BIO103).

The mdx animals received daily, per os, either the vehicle or BIO101 (50 mg/kg*day) or BIO103 (50 mg/kg*day). The results of the quantification of the number of muscle fibres after two months of daily exposure are shown in FIG. 10B.

It is observed that the mdx animals that received BIO101 or BIO103 exhibit greater vascularisation than the mdx animals receiving the vehicle. It is observed that BIO101 tends to improve the number of vessels per muscle fibre by an increase of 14.1% (p=0.13, unpaired t test). In a more pronounced way, BIO103 significantly increases, by 28.2% (p=0.006, unpaired t test) muscular vascularisation compared to the untreated mdx animals (vehicle).

Treatments with BIO101 and particularly with BIO103 increase the number of vessels per muscle fibre.

These results demonstrate an efficacy of BIO101 and BIO103 on various muscle parameters in vitro and in vivo. Indeed, treating muscle cells of patients suffering from DMD with BIO101 or BIO103 demonstrates that they enhance differentiation, and the energy metabolism (mitochondrial respiration) of the cells and that they are capable of increasing muscle vascularisation in vivo, which is important for proper muscle function.

Conclusion

In view of the properties of BIO101 and BIO103 on muscle function and on the onset of myocardial and skeletal muscle fibrosis in mammals suffering from a myopathy, the use of BIO101 and BIO103 may therefore be proposed, alone or alongside a treatment aimed at correcting the effects of a genic alteration, to preserve muscle function, particularly muscle strength and exertion tolerance and thus slow down the progression of myopathies which result in deterioration of said muscle function, and more particularly the onset of fibrosis. These myopathies include genetic myopathies, particularly Duchenne muscular dystrophy.

Bibliography

Barnabei M. S., Martindale J.M., Townsend D., Metzger J. M. (2011). Exercise and muscular dystrophy: implications and analysis of effects on musculoskeletal and cardiovascular systems. Compr Physiol. 2011 July; 1(3):1353-63

Brigstock D R 2010. Connective tissue growth factor (CCN2, CTGF) and organ fibrosis: lessons from transgenic animals. *J Cell Commun Signal.* 4 (1): 1-4;

Bulfield G., Siller W. G., Wight P. A., Moore K. J. (1984). X chromosome-linked muscular dystrophy (mdx) in the mouse. Proc. Natl. Acad. Sci. USA 81, 1189-1192.

Ferry A, Amiridis I, Rieu M. 1992. Glycogen depletion and resynthesis in the rat after downhill running. *Eur J Appl Physiol Occup Physiol* 64(1): 32-35.

Ferry A, Rieu P, Le Page C, Elhabazi A, Laziri F, Rieu M.1993. Effect of physical exhaustion and glucocorticoids (dexamethasone) on T-cells of trained rats. *Eur J Appl Physiol Occup Physiol* 66(5): 455-460.

Gorelick-Feldman J, MacLean D, Ilic N, Poulev A, Lila MA, Cheng D, Raskin I. 2008. Phytoecdysteroids increase protein synthesis in skeletal muscle cells. *J Agric Food Chem*56: 3532-3537.

Hadj-Said W, Bangratz M, Vignaud A, Chatonnet A, Butler-Browne G, Nicole S, Agbulut O, Ferry A. 2012. Effect of locomotor training on muscle performance in the context of nerve-muscle communication dysfunction. *Muscle Nerve* 45(4): 567-577.

Hay N and Sonenberg N. (2004). Upstream and downstream of mTOR. Genes Development 18: 1926-1945.

Huebner K D, Jassal D S, Halevy O, Pines M and Anderson JE. (2008). Functional resolution of fibrosis in mdx mouse dystrophic heart and skeletal muscle by halofuginone. Am J Physiol Heart Circ Physiol. 294(4): H1550-61.

Lafont R, Raynal S, Dioh W, Veillet S, Lepifre F, Durand J D. 2014. Produits derives de la 20-hydroxyecdysone et leur utilisation dans la préparation de médicaments. Application FR3021318 (filed 20/05/2014).

Lawrence M M. 2012. Ajuga turkestanica as a countermeasure against sarcopenia and dynapenia. Ms thesis, Appalachian State University.

Loufrani L, Dubroca C, You D, Li Z, Levy B, Paulin D et al. (2004). Absence of dystrophin in mice reduces NO-dependent vascular function and vascular density: total recovery after a treatment with the amino-glycoside gentamicin. Arterioscler. Thromb. Vasc. Biol. 24: 671-676.

Matsakas A, Yadav V, Lorca S, Narkar V. (2013). Muscle ERR gamma mitigates Duchenne muscular dystrophy via metabolic and angiogenic reprogramming. FASEB J. 27: 4004-4016.

Murphy S., Dowling P., Zweyer M., Mundegar R., Henry M., Meleady P., Swandulla D., Ohlendieck K. (2016). Proteomic analysis of dystrophin deficiency and associated changes in the aged mdx-4cv heart model of dystrophinopathy-related cardiomyopathy. J. Proteomics, 145,24-36

Palladino M, Gatto I, Neri V, Straino S, Smith R C, Silver M et al. (2013). Angiogenic impairment of the vascular endothelium: a novel mechanism and potential therapeutic target in muscular dystrophy. Arterioscler. Thromb. Vasc. Biol. 33: 2867-2876.Rando TA. (2001). Role of nitric oxide in the pathogenesis of muscular dystrophies: a "two hit" hypothesis of the cause of muscle necrosis. Microsc. Res. Tech. 55: 223-235.

Rittié L. (2017). Method for Picrosirius Red-Polarization Detection of Collagen Fibers in Tissue Sections. Methods Mol Biol. 1627: 395-407.

Roffe S, Hagai Y, Pines M, Halevy O. (2010). Halofuginone inhibits Smad3 phosphorylation via the Pl3K/Akt and MAPK/ERK pathways in muscle cells: effect on myotube fusion. Exper Cell Res. 316(6): 1061-1069.

Schuh R A, Jackson K C, Khairallah R J, Ward C W, Spangenburg E E. (2012). Measuring mitochondrial respiration in intact single muscle fibers. Am J Physiol Regul Integr Comp Physiol. 302(6): R712-R719.

Shi S., Hoogaars W. M., de Gorter D. J., van Heiningen S. H., Lin H. Y., Hong C. C., Kemaladewi D. U., Aartsma-Rus A., ten Dijke P., 't Hoen P. A. (2011). BMP antagonists enhance myogenic differentiation and ameliorate the dystrophic phenotype in a DMD mouse model. Neurobiol Diseases 41(2), 353-360

Sicinski P, Geng Y, Ryder-Cook A S, Barnard E A, Darlison M G, Barnard P J. 1989. The molecular basis of muscular dystrophy in the mdx mouse: a point mutation. *Science* 244 (4912), 1578-1580.

Simakin SYu, Panyushkin V V, Portugalov S N, Kostina L V, Martisorov E G. 1988. Combined application of preparation Ecdysten. Science Bulletin N° 2, 29-31.

Song Y, Yao S, Liu Y, Long L, Yang H, Li Q, Liang J, Li X, Lu Y, Zhu H, Zhang N. 2017. Expression levels of TGF-β1 and CTGF are associated with the severity of Duchenne muscular dystrophy. Exp Ther Med 13(4): 1209-1214.

Syrov V N. 2000. Comparative experimental investigations of the anabolic activity of ecdysteroids and steranabols. Pharm Chem Journal 34(4):193-197.

Tóth N, Szabó A, Kacsala P, Heger J, Zádor E. 2008. 20-Hydroxyecdysone increases fiber size in a muscle-specific fashion in rat. *Phytomedicine* 15: 691-698.

Turgeman T, Hagai Y, Huebner K, Jassal D S, Anderson J E, Genin O, Nagler A, Halevy O, Pines M. (2008). Prevention of muscle fibrosis and improvement in muscle performance in the mdx mouse by halofuginone. Neuromuscul Disord. 18(11): 857-868

Turk R, Sterrenburg E, van der Wees C G, de Meijer E J, de Menezes R X, Groh S, Campbell K P, Noguchi S, van Ommen G J, den Dunnen J T, 't Hoen PA. (2006). Common pathological mechanisms in mouse models for muscular dystrophies. FASEB J. 20(1): 127-129.Wang X, McLennan S V, Allen T J, Twigg S M. 2010. Regulation of pro-inflammatory and pro-fibrotic factors by CCN2/CTGF in H9c2 cardiomyocytes. *J Cell Comm. Signal* 4: 15-23

Yin Z., Ren J., Guo W. (2014), Sarcomeric protein isoform transitions in cardiac muscle: A journey to heart failure. *Biochim Biophys Acta.* 1852(1):47-52

The invention claimed is:

1. A method of treatment of Duchenne muscular dystrophy (DMD) and/or Becker muscular dystrophy (BMD), comprising the step of administering to a subject in need thereof an effective amount of a compound selected from:
   a) 20-hydroxyeedysone;
   a compound of formula (II):

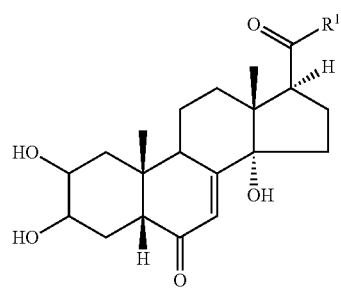

(II)

wherein:
R$^1$ is chosen from: a group (C$_1$-C$_6$)W(C$_1$-C$_6$); a group (C$_1$-C$_6$)W(C$_1$-C$_6$)W(C$_1$-C$_6$); a group (C$_1$-C$_6$)W(C$_1$-C$_6$)CO$_2$(C$_1$-C$_6$); a group (C$_1$-C$_6$)A, A representing a heterocycle optionally substituted by a group of the type OH, OMe, (C$_1$-C$_6$), N(C$_1$-C$_6$), CO$_2$(C$_1$-C$_6$); a CH$_2$Br group;
W being a heteroatom chosen from N, O, and S; and a compound of formula (III):

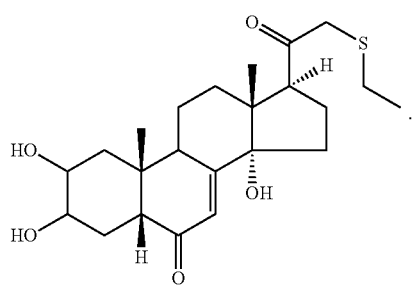

(III)

2. The method according to claim 1, wherein the Duchenne muscular dystrophy (DMD) and/or the Becker muscular dystrophy (BMD) induces an impairment of a muscle function.

3. The method according to claim 2, wherein the muscle function is striated skeletal muscle function or myocardium function.

4. The method according to claim 2, wherein the impairment is myocardial hypertrophy.

5. The method according to claim 2, wherein the muscle function is at least in part impaired by a progressive onset of fibrosis.

6. The method according to claim 1, wherein mitochondrial respiration of muscle cells is increased.

7. The method according to claim 1, wherein a number of vessels per muscle fibre is increased.

8. The method according to claim 1, wherein myoblast differentiation into myotubes is increased.

9. The method according to claim 1, wherein the 20-hydroxyecdysone is a compound of formula (I):

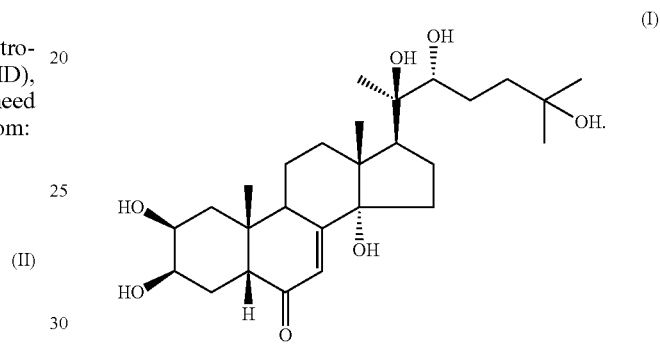

(I)

10. The method according to claim 1, wherein the 20-hydroxyecdysone is a plant extract, or an extract from a part of a plant, said plant being chosen from plants containing at least 0.5% 20-hydroxyecdysone of formula (I) in dry weight of said plant, said plant extract, or said extract from said part of said plant, comprising at least 95% 20-hydroxyecdysone of formula (I);
wherein the 20-hydroxyecdysone of formula (I) is:

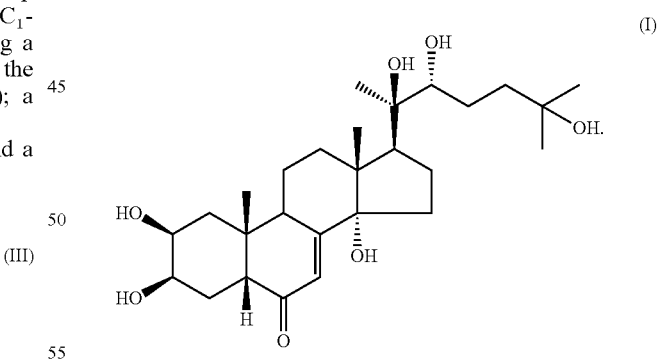

(I)

11. The method according to claim 10, wherein the extract comprises between 0 and 0.05%, in dry weight of the extract, of impurities liable to affect the safety, availability or efficacy of a pharmaceutical application of said extract.

12. The method according to claim 10, wherein the plant is chosen from *Stemmacantha carthamoides, Cyanotis arachnoidea* and *Cyanotis vaga*.

13. The method according to claim 1, wherein the 20-hydroxyecdysone is a *Stemmacantha carthamoides* root extract comprising at least 95% 20-hydroxyecdysone of formula (I).

14. The method according to claim 1, wherein in the compound of formula (II):

R$^1$ is chosen from: a group $(C_1-C_6)W(C_1-C_6)$; a group $(C_1-C_6)W(C_1-C_6)W(C_1-C_6)$; a group $(C_1-C_6)W(C_1-C_6)CO_2(C_1-C_6)$; a group $(C_1-C_6)A$, A representing a heterocycle optionally substituted by a group of the type OH, OMe, $(C_1-C_6)$, $N(C_1-C_6)$, $CO_2(C_1-C_6)$, W being a heteroatom chosen from N, O and S.

15. The method according to claim 1, wherein the compound of formula (II) is chosen from:
- No. 1: (2S,3R,5R,10R,13R,14S,17S)-2,3,14-trihydroxy-10,13-dimethyl-17-(2-morpholinoacetyl)-2,3,4,5,9,11,12,15,16,17-decahydro-1H-cyclopenta[a]phenanthren-6-one;
- No. 2: (2S,3R,5R,10R,13R,14S,17S)-2,3,14-trihydroxy-17-[2-(3-hydroxypyrrolidin-1-yl)acetyl]-10,13-dimethyl-2,3,4,5,9,11,12,15,16,17-decahydro-1H-cyclopenta[a]phenanthren-6-one;
- No. 3: (2S,3R,5R,10R,13R,14S,17S)-2,3,14-trihydroxy-17-[2-(4-hydroxy-1-piperidyl)acetyl]-10,13-dimethyl-2,3,4,5,9,11,12,15,16,17-decahydro-1H-cyclopenta[a]phenanthren-6-one;
- No. 4: (2S,3R,5R,10R,13R,14S,17S)-2,3,14-trihydroxy-17-[2-[4-(2-hydroxyethyl)-1-piperidyflacetyl]-10,13-dimethyl-2,3,4,5,9,11,12,15,16,17-decahydro-1H-cyclopenta[a]phenanthren-6-one;
- No. 5: (2S,3R,5R,10R,13R,14S,17S)-17-[2-(3-dimethylaminopropyl(methyl)amino)acetyl]-2,3,14-trihydroxy-10,13-dimethyl-2,3,4,5,9,11,12,15,16,17-decahydro-1H-cyclopenta[a]phenanthren-6-one;
- No. 6: 2-[2-oxo-2-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-l'17-yl[ethyl]ethyl sulfanylacetate;
- No. 7: (2S,3R,5R,10R,13R,14S,17S)-17-(2-ethylsulfanylacetyl)-2,3,14-trihydroxy-10,13-dimethyl-2,3,4,5,9,11,12,15,16,17-decahydro-1H-cyclopenta[a]phenanthren-6-one; and
- No. 8: (2S,3R,5R,10R,13R,14S,17S)-2,3,14-trihydroxy-17-[2-(2-hydroxyethylsulfanyl)acetyl]-10,13-dimethyl-2,3,4,5,9,11,12,15,16,17-decahydro-1H-cyclopenta[a]phenanthren-6-one.

16. The method according to claim 10, wherein said plant extract, or said extract from said part of said plant, comprises at least 97% 20-hydroxyecdysone of formula (I).

17. The method according to claim 13, wherein the *Stemmacantha carthamoides* root extract comprises at least 97% 20-hydroxyecdysone of formula (I).

\* \* \* \* \*